United States Patent
Costabile

(10) Patent No.: US 8,753,367 B1
(45) Date of Patent: Jun. 17, 2014

(54) DEVICE AND METHOD FOR ATTACHING HAIR

(71) Applicant: James Costabile, Clark, NJ (US)

(72) Inventor: James Costabile, Clark, NJ (US)

(*) Notice: Subject to any disclaimer, the term of this patent is extended or adjusted under 35 U.S.C. 154(b) by 0 days.

(21) Appl. No.: 13/723,778

(22) Filed: Dec. 21, 2012

(51) Int. Cl.
*A61F 2/10* (2006.01)

(52) U.S. Cl.
USPC .................. 606/187; 623/15.11; 132/201

(58) Field of Classification Search
CPC ....... A41G 5/0053; A41G 5/0073; A61F 2/10
USPC ................. 606/187, 232; 623/15.11; 132/201
See application file for complete search history.

(56) References Cited

U.S. PATENT DOCUMENTS

| | | | |
|---|---|---|---|
| 1,378,147 A | 5/1921 | Tapscott | |
| 1,490,479 A | 4/1924 | Noel | |
| 3,643,658 A | 2/1972 | Steinemenan | |
| 3,662,766 A | 5/1972 | Maassen et al. | |
| 3,694,819 A | 10/1972 | Meyer | |
| 3,811,425 A * | 5/1974 | Widdifield | 606/187 |
| 3,858,247 A | 1/1975 | Bauman | |
| 3,862,453 A | 1/1975 | Widdifield | |
| 3,877,570 A | 4/1975 | Barry | |
| 4,037,274 A | 7/1977 | Agosta | |
| 4,050,100 A | 9/1977 | Barry | |
| 4,144,876 A | 3/1979 | DeLeo | |
| 4,265,246 A | 5/1981 | Barry | |
| 4,676,802 A * | 6/1987 | Tofield et al. | 604/332 |
| 4,753,656 A | 6/1988 | Tofield et al. | |
| 4,870,957 A | 10/1989 | Goble et al. | |
| 4,969,903 A | 11/1990 | Valle | |
| 5,370,662 A | 12/1994 | Stone et al. | |
| 5,545,224 A * | 8/1996 | Israelsen | 128/898 |
| 5,697,979 A | 12/1997 | Pignataro | |
| 5,741,336 A | 4/1998 | Fraser | |
| 5,911,721 A * | 6/1999 | Nicholson et al. | 606/326 |
| 6,090,142 A * | 7/2000 | Grifka et al. | 623/15.11 |
| 6,561,197 B2 | 5/2003 | Harrison | |
| 7,311,720 B2 * | 12/2007 | Mueller et al. | 606/213 |
| 2002/0179108 A1 | 12/2002 | Harrison | |
| 2005/0267479 A1 * | 12/2005 | Morgan et al. | 606/73 |
| 2007/0106394 A1 | 5/2007 | Chen | |
| 2009/0056730 A1 * | 3/2009 | Wilson et al. | 132/53 |
| 2009/0199861 A1 | 8/2009 | Paris | |
| 2010/0037908 A1 | 2/2010 | Hatcher et al. | |

* cited by examiner

*Primary Examiner* — Corrine M McDermot
*Assistant Examiner* — Shaun L David
(74) *Attorney, Agent, or Firm* — Arthur Jacob

(57) ABSTRACT

A fitting and a method for utilizing one or more of such fittings are described for securing supplemental hair to a person's head, along the outer surface of the person's scalp, to create an enhanced, natural appearance independent of the population and location of any natural hair on the person's head. Each fitting includes a base member having a resiliently flexible flange, and a post rising from the flange and carrying a flexible filament establishing a loop providing a lateral path for a ligature. Each base member is embedded beneath the outer surface of the person's scalp to secure the corresponding fitting at a selected strategic location on the person's head with the filament projecting from the outer surface to provide a corresponding attachment site. Supplemental hair is juxtaposed with and secured to each filament with a corresponding ligature passed through the loop of each corresponding filament.

13 Claims, 5 Drawing Sheets

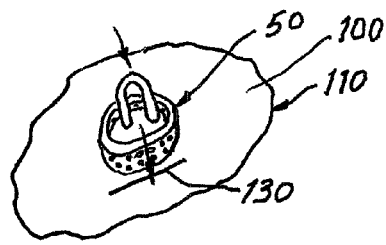
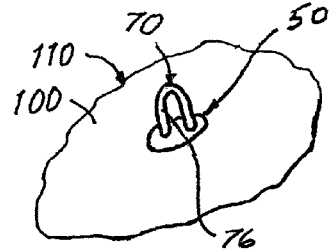
FIG. 10  FIG. 11
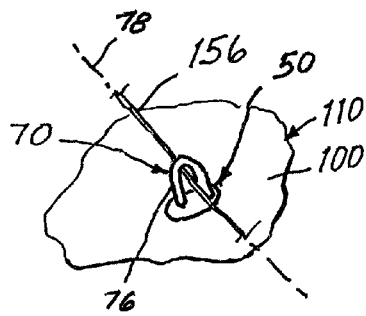
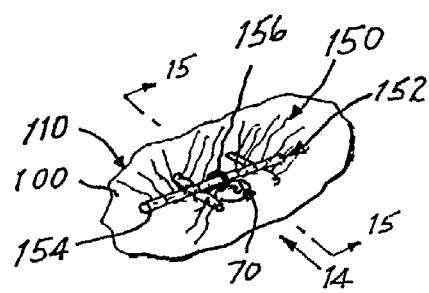
FIG. 12  FIG. 13
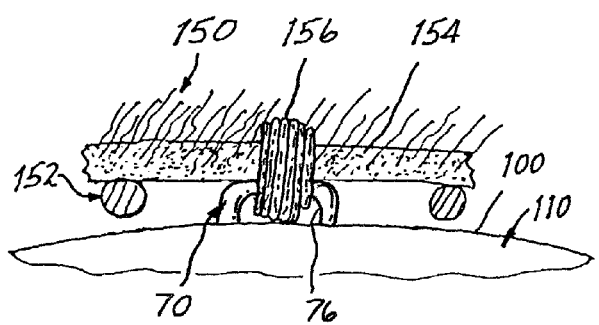
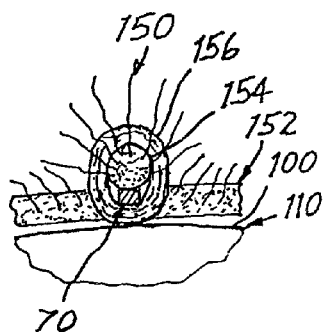
FIG. 14  FIG. 15

DEVICE AND METHOD FOR ATTACHING HAIR

The present invention relates generally to the attachment of hair to the human head and pertains, more specifically, to a device and method for securing hair to a human head, usually as a supplement to a person's natural hair, so as to provide an enhanced, natural appearance which will last over an extended service life.

A well-received method currently in use for supplementing a person's natural hair to provide an enhanced, natural appearance consists of securing supplemental hair to existing natural hair, with care being taken to assure that melding of the supplemental hair with the natural hair is accomplished so skillfully as to go undetected by ordinary observation. While highly effective, the method suffers a drawback in that with the passage of time, the natural hair will grow out, taking with it the attached supplemental hair and adversely affecting the desired natural look. In addition, the attachment locations may become exposed to view, with the concomitant defeat of the natural look sought by the person. In order to overcome these drawbacks, adjustments are made from time to time to restore the natural appearance. Further, this current method, while highly desirable and widely pursued, requires that enough natural hair be available to provide a suitable number of strategically located sites for the attachment of supplemental hair to attain the desired, natural appearance.

In my earlier patents, U.S. Pat. Nos. 7,862,613 and 7,993,400, the full disclosures of which are incorporated herein by reference thereto, there is described a device and method for attaching hair which accomplishes the securement of supplemental hair to a person's head, while avoiding the above-described drawbacks. The present invention accomplishes the securement of supplemental hair to a persons's head, while attaining further objects and advantages, some of which are summarized as follows: Provides a human head with one or more attachment sites for securing hair at strategic locations to supplement natural hair present on the head and attain an enhanced appearance independent of the population and location of natural hair present on the head with increased ease, safety and comfort; facilitates further the attachment of supplemental hair to a human head at one or more locations selected for best attaining a natural and long-enduring aesthetic appearance; enables the establishment of strategically located hair attachment sites, utilizing more simple, even less minimally invasive procedures for safety, comfort and increased longevity; establishes an aesthetically pleasing appearance capable of even longer-term service without requiring periodic adjustments to maintain the pleasing appearance; facilitates further the conduct of regular hair care without the necessity for extraordinary procedures to compensate for the presence of secured supplemental hair; simplifies even further the placement and attainment of a secure and reliable attachment of supplemental hair to a person's head utilizing a minimally invasive procedure that promotes rapid healing and reduces any tendency toward failure over an extended service life; encourages further adoption of the attachment of supplemental hair to enhance appearance; provides for a more reliable attachment of supplemental hair for exemplary long-term performance.

The above objects and advantages, as well as further objects and advantages, are attained by the present invention, which may be described briefly as a fitting for placement at a selected location on a person's head, embedded beneath the outer surface of the person's scalp to secure the fitting at the selected location, and enable securement of hair to the person's head, the fitting comprising: a base member extending in longitudinal and lateral directions for placement between the outer surface of the scalp and the underlying bone of the person's skull, the base member having a flange for being spaced a first altitudinal distance from the outer surface and a second altitudinal distance from the bone, a post integral with the flange and extending along an altitudinal axis from the flange to an apical end, the post having a length corresponding substantially to the first altitudinal distance, the flange being flexible for selective folding away from a deployed position, wherein the flange extends radially with respect to the altitudinal axis, to a folded position, wherein the flange extends substantially parallel to the altitudinal axis for facilitating insertion of the base member through a minimal incision in the scalp; and a filament extending from the apical end of the post to establish a loop projecting altitudinally from the post, the loop providing an open path extending in lateral directions, the filament being flexible relative to the post, such that upon embedding the base member beneath the outer surface of the scalp, the loop will project altitudinally from the scalp for reception of a ligature for securing hair to the fitting, with the loop being capable of flexing while the post remains stationary, and the apical end located in substantial juxtaposition with the outer surface of the scalp.

In addition, the present invention provides a method for securing supplemental hair to a person's head, along the outer surface of the person's scalp, to create an enhanced natural appearance independent of any natural hair on the person's head, the method comprising: selecting at least one strategic location on the person's head; placing at least one fitting at the selected location, the fitting including a base member extending in longitudinal and lateral directions, the base member having a flange, and a post integral with the flange and extending along an altitudinal axis from the flange to an apical end, the post having a predetermined length, the flange being flexible for selective folding away from a deployed position, wherein the flange extends radially with respect to the altitudinal axis, to a folded position, wherein the flange extends substantially parallel to the altitudinal axis, and a filament extending from the apical end of the post to establish a loop projecting altitudinally from the post, the loop providing an open path extending in lateral directions, the filament being flexible relative to the post; folding the flange from the deployed position to the folded position; embedding the flange beneath the outer surface of the person's scalp with the flange placed between the outer surface of the scalp and the underlying bone of the person's skull, spaced from both the outer surface and the bone, to secure the fitting at the selected strategic location with the filament projecting altitudinally from the scalp to expose the loop for reception of a ligature; juxtaposing supplemental hair with the loop; passing a ligature along the open path through the loop; and securing the juxtaposed supplemental hair to the filament with the ligature.

The present invention will be understood more fully, while still further objects and advantages will become apparent, in the following detailed description of preferred embodiments of the invention illustrated in the accompanying drawing, in which:

FIGS. 10 through 13 are pictorial views demonstrating a method practiced in accordance with the present invention;

FIG. 14 is an enlarged, somewhat diagrammatic view taken in the direction of the arrow 14 in FIG. 13; and FIG. 15 is an enlarged, somewhat diagrammatic cross-sectional view taken along the one 15-15 of FIG. 13.

Figure 1:
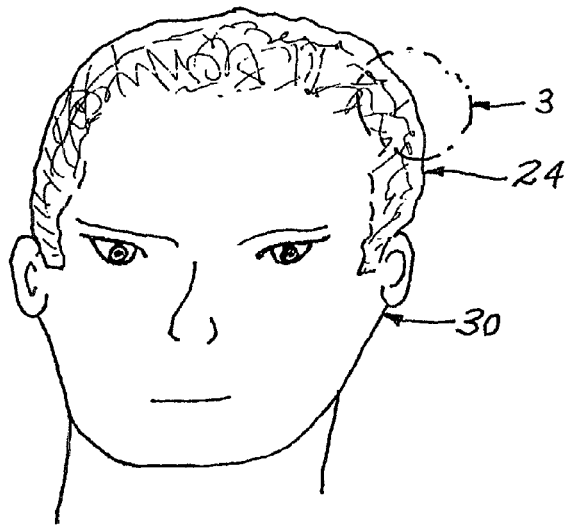
FIG. 1 is a pictorial illustration showing a person who has been subjected to a currently-practiced procedure.
Figure 2:
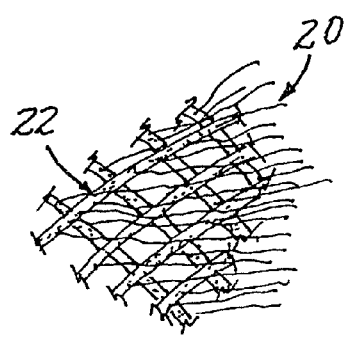
FIG. 2 is a fragmentary pictorial illustration of a form in which supplemental hair is made available currently.
Figure 3:
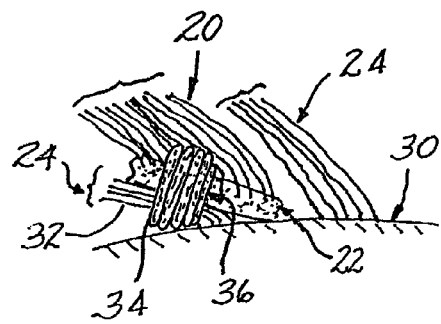
FIG. 3 is an enlarged diagrammatic fragmentary cross-sectional view illustrating the results of a currently-practiced method for attaching supplemental hair to existing natural hair at a site indicated by the arrow 3 in FIG. 1.
Figure 4:
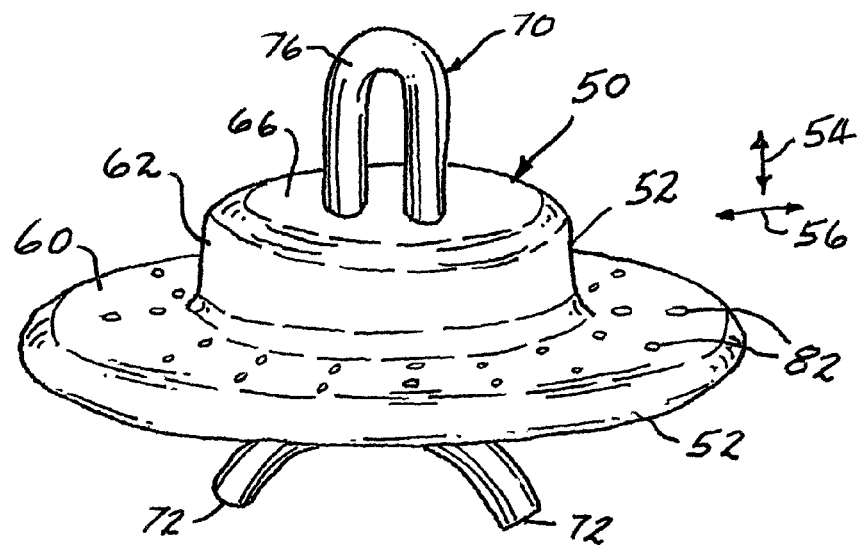
FIG. 4 is a front, top pictorial view of a device constructed in accordance with the present invention.
Figure 5:
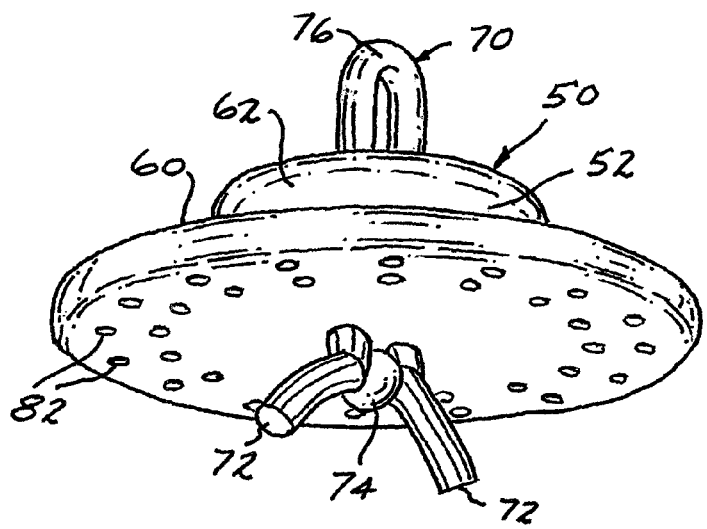
FIG. 5 is a front, bottom pictorial view of the device of FIG. 4.
Figure 6:
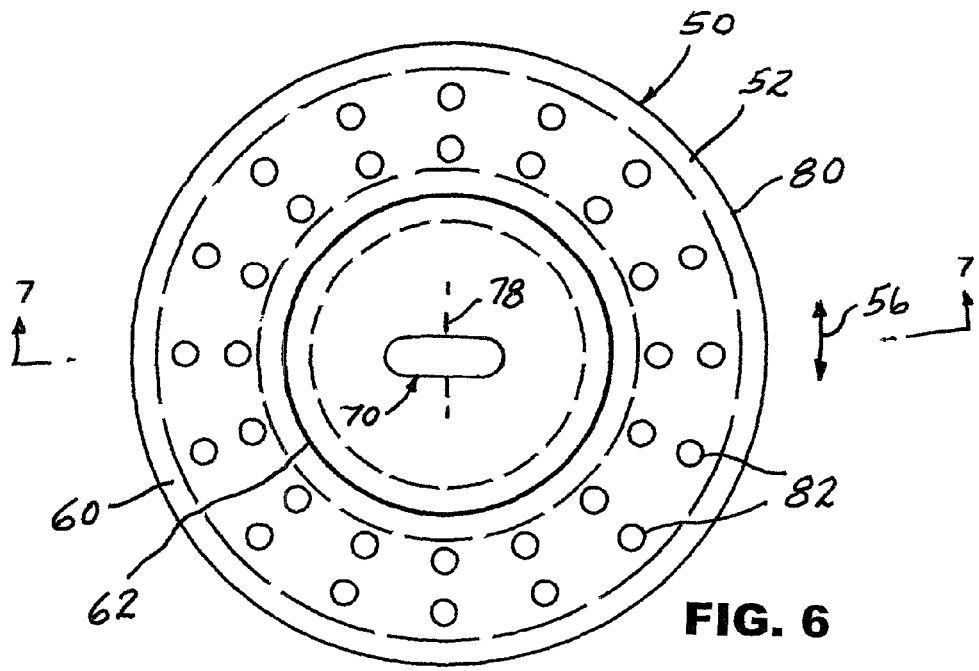
FIG. 6 is a top plan view of the device of FIG. 4.

Referring now to the drawing, and especially to FIGS. 1 through 3 thereof, in a currently-practiced procedure, supplemental hair 20, which is woven or otherwise affixed to a web-like basal member 22, is attached to existing natural hair 24 on a person's head 30 to supplement the natural hair 24 and provide an enhanced, fuller, more aesthetically pleasing appearance. Attachment is attained by securing the basal member 22 to tufts, such as tuft 32, of natural hair 24, as by threads 34 at locations 36 selected to deploy the supplemental hair 20 over the head 30 so as to meld the supplemental hair 20 with the existing natural hair 24 and emulate a natural disposition of hair, while the locations 36 themselves skillfully are hidden from view by surrounding natural hair 38 to complete the desired natural look. However, as time passes, the natural hair 24 in tuft 32 will grow out, carrying with it the attachment locations 36 and adversely affecting the desired natural appearance. In addition, the locations 36 may become exposed to view, further compromising a natural look. Such eventual growth effectively will destroy the sought-after natural appearance and gives rise to a requirement for adjustments to be made from time to time to once again hide attachment locations 36 and regain the desired natural appearance.

Turning now to FIGS. 4 through 7, the present invention provides a fitting 50 constructed for placement at a selected location on a person's head, as will be demonstrated below, embedded just beneath the outer surface of the person's scalp, to provide a site for securement of supplemental hair, independent of any natural hair present on the person's head. To that end, fitting 50 includes a base member 52 extending in longitudinal directions 54 and in lateral directions 56, and having a flange 60 and a post 62. Post 62 is integral with, and preferably unitary with, the flange 60 and extends along an altitudinal axis 64, from flange 60 to an apical end 66, post 62 having a length L. A filament 70 is affixed to the base member 52 and projects altitudinally from post 62. In the illustrated embodiment, filament 70 follows an inverted U-shaped configuration and extends through base member 52 adjacent both ends 72 of the filament 70, and a knot 74 adjacent the ends 72 secures the filament 70 in place on the base member 52, while establishing a loop 76 providing an open path 78 extending through the loop 76 in the lateral directions 56.

In the preferred embodiment, base member 52 is molded of a resiliently flexible biocompatible material, one such material being a high consistency silicone, such as that sold under the trademark NUSIL, having a durometer of about 55 with ultra-high tear strength. Filament 70 advantageously is constructed of a polypropylene surgical suture material, preferably in the form of a monofilament, non-absorbable suture having high tensile strength, providing no significant changes in vivo and being unaffected or weakened by tissue enzymes. Knot 74 is a surgeon's knot, providing extra surface friction characteristics that reduce the possibility of loosening, especially during assembly. While the two different materials provide the base member 52 and the filament 70, respectively, with corresponding exemplary properties, other material choices are feasible, and are known to those skilled in the art of biocompatible materials. In particular, a variety of synthetic polymeric materials are available which can enable molding of the base member 52 and the filament 70 in a unitary structure of a single material.

Typically, flange 60 of base member 52 is provided with a circular perimeter 80 having a diameter D of about 0.5 inch, while height H of base member 52 is about 0.12 inch, and flange 60 has a thickness T of about 0.04 inch. A plurality of openings 82 extend altitudinally through flange 60, rendering flange 60 foraminate, for purposes to be described below.

With reference now to FIGS. 8 through 15, as well as to FIGS. 4 through 7, a person 90 has natural hair 92 growing about the person's head 94 and desires to supplement the natural hair 92 to establish an enhanced appearance provided by a fuller head of hair. In the practice of the method of the present invention, supplemental hair for that purpose is secured to the person's head 94 as follows: A plurality of fittings 50 are embedded beneath outer surface 100 of the person's scalp 110 to provide attachment sites 112 for the attachment of supplemental hair. The location of each attachment site 112 is selected in relation to existing natural hair 92 to assure melding of the supplemental hair with the natural hair 92 and to attain a natural appearance in which the attachment sites 112 will be hidden from view.

Returning briefly now to FIG. 7, and in connection with the placement of each fitting 50 at an attachment site 112, the resiliently flexible characteristics of the material of flange 60 enables selective folding of the flange 60 from a deployed position, as shown in full lines in FIG. 7, wherein the flange 60 extends radially with respect to the altitudinal axis 64, to a folded position, as illustrated in phantom in FIG. 7, wherein the flange 60 extends substantially parallel with the direction of altitudinal axis 64. In this manner, the diametric span S across base member 52, when flange 60 is in the folded position, is minimized and insertion of the fitting 50 at an attachment site 112 is facilitated, as will be described below.

Figure 7:
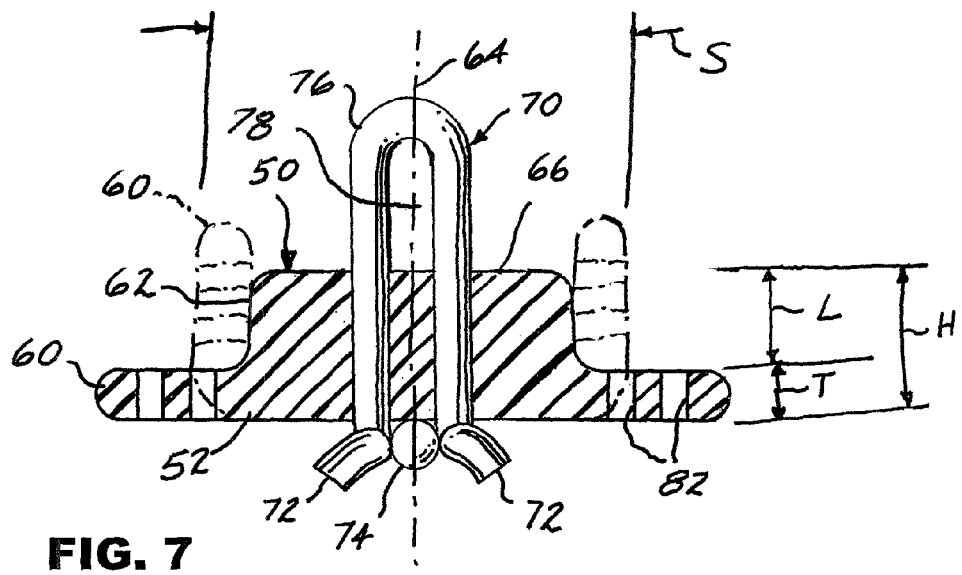
FIG. 7 is a cross-sectional view taken along line 7-7 of FIG. 6.
Figure 8:
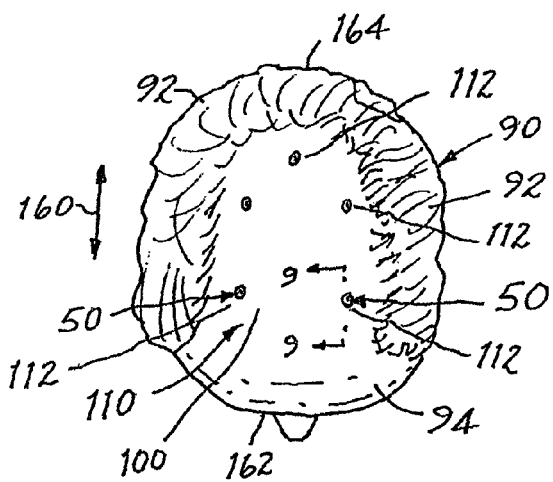
FIG. 8 is a top plan view of the head of a person showing devices of FIG. 4 installed in accordance with the method of the present invention.
Figure 9:
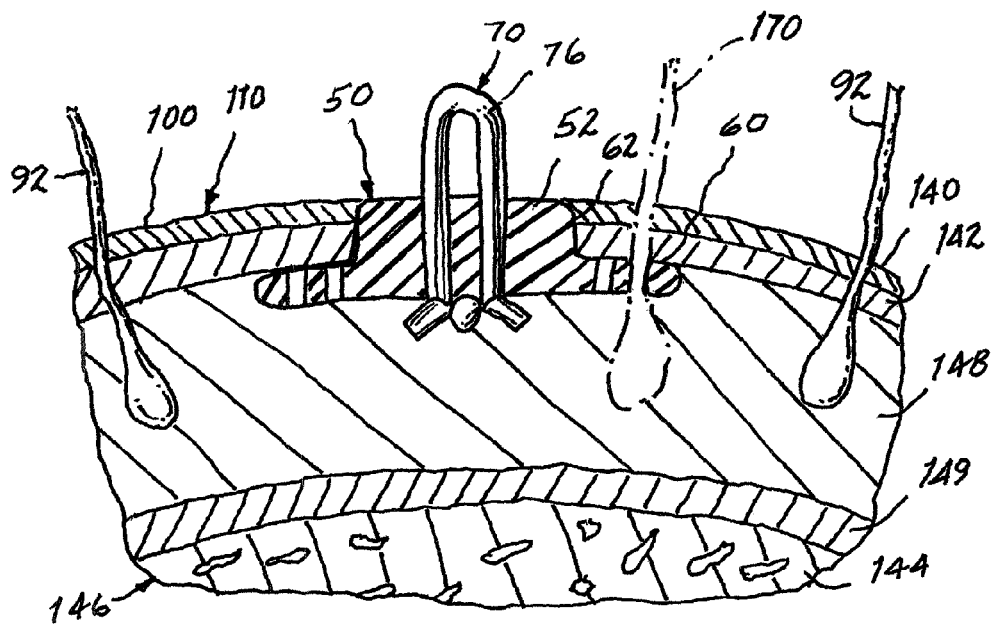
FIG. 9 is a much enlarged, somewhat diagrammatic fragmentary cross-sectional view taken along line 9-9 of FIG. 8.

Each fitting 50 is embedded beneath the outer surface 100 of the scalp 110 by making a relatively short and shallow, minimally invasive incision 130 in the scalp 110, as seen in FIG. 10, incision 130 having a length approximately equal to the diametric span S of the flange 60 when the flange 60 is in the folded position, also illustrated in phantom in FIG. 7, and a depth which penetrates the epidermis 140 and extends through the derma 142 of scalp 110. Base member 52 then is inserted, as seen in FIG. 11, and placed beneath the epidermis 140 and the derma 142, preferably juxtaposed with the derma 142. Once the base member 52 is so placed, a resilient biasing force established by the resiliently flexible characteristics of the material of flange 60 serves to return the flange 60 to the deployed position, and the fitting 50 is secured within the scalp 110, with the flange 60 lying below the outer surface 100, spaced away from the outer surface 100 by a first altitudinal distance determined substantially by the length L of post 62, and spaced away from the bone 144 of the person's skull 146 over a second altitudinal distance by subcutaneous cellular tissue 148 and muscle tissue 149, as seen in FIG. 9, enabling securement of the fitting 50 with a minimally invasive procedure. At the same time, the apical end 66 of the post 62 is placed in juxtaposition with outer surface 100, and filament 70 is exposed. Once the fitting 50 is seated, the incision 130 is closed over the flange 60 and around the post 62, so that the filament 70 projects above the outer surface 100 of the scalp 110 and rises from the scalp 110 to expose loop 76, as seen in FIG. 11.

With a loop 76 exposed at each attachment site 112, supplemental hair 150 is attached to each fitting 50. Thus, as before, supplemental hair 150 is affixed to a web-like basal member 152 of strands 154 which are available for securement to a filament 70 by a ligature in the form of a thread 156 passed through loop 76, along path 78, as seen in FIG. 12, and then around a strand 154, as seen in FIG. 13. Because securement of supplemental hair 150 now is accomplished independent of the existing natural hair 92, attachment sites 112 can be placed at locations selected skillfully, independent of the population and location of natural hair 92, to assure appropriate melding of supplemental hair 150 with natural hair 92 for an aesthetically pleasing enhanced natural look. In addition, should there be a dearth of available natural hair 92, fittings 50 can be located, independent of existing natural hair 92, to provide for the attachment of supplemental hair 150 for creating a full and natural-appearing head of hair.

The characteristics of fitting 50 facilitates the embedding of fittings 50 wherever necessary throughout the head 94 of person 90. Thus, the resiliently flexible nature of flange 60 enables the flange 60 to substantially follow the contour of the head 94 and assures a firm seating of each fitting 50 at any selected attachment site 112. Further, the highly flexible nature of filament 70 not only establishes a substantially unobtrusive attachment site 112, to assist in hiding each fitting 50 from view, but provides a ready transition between the outer surface 100 of scalp 110 and the filament 70, offering little or no resistance to the conduct of regular hair maintenance, such as cleansing and grooming. The very limited projection of the filament 70 above the outer surface 100 of scalp 110, coupled with the highly flexible nature of filament 70, renders the filament 70 unobtrusive and enables cleansing and grooming without significant interference from fittings 50. Again, the highly flexible nature of filament 70 enables the filament 70 to present essentially no impediment to combs and brushes ordinarily run across the head 94, and through the hair on the head 94, in any selected direction, thus requiring no specific orientation of fitting 50 upon insertion at an attachment site 112. At the same time, the less-flexible post 62 assures that the fitting 50 remains securely anchored in place, thereby avoiding deleterious effects upon the scalp that might otherwise occur as a result of excessive displacements of post 62, and base member 52, over the service life of a fitting 50.

With supplemental hair 150 secured to each fitting 50, rather than to existing hair 92, the attachment sites 112 will remain unaffected by growth over time of the natural hair 92. Thus, adjustments over time no longer are necessary in order to maintain the natural look sought by the addition of supplemental hair 150. It is noted that the foraminate construction of base 52 enables natural hair to grow through the base member 52 where hair follicles are present for such growth, as illustrated in phantom at 170 in FIG. 9.

It will be seen then that the present invention attains all of the objects and advantages summarized above, namely: Provides a human head with one or more attachment sites for securing hair at strategic locations to supplement natural hair present on the head and attain an enhanced appearance independent of the population and location of natural hair present on the head with increased ease, safety and comfort; facilitates further the attachment of supplemental hair to a human head at one or more locations selected for best attaining a natural and long-enduring aesthetic appearance; enables the establishment of strategically located hair attachment sites, utilizing more simple, even less minimally invasive procedures for safety, comfort and increased longevity; establishes an aesthetically pleasing appearance capable of even longer-term service without requiring periodic adjustments to maintain the pleasing appearance; facilitates further the conduct of regular hair care without the necessity for extraordinary procedures to compensate for the presence of secured supplemental hair; simplifies even further the placement and attainment of a secure and reliable attachment of supplemental hair to a person's head utilizing a minimally invasive procedure that promotes rapid healing and reduces any tendency toward failure over an extended service life; encourages further adoption of the attachment of supplemental hair to enhance appearance; provides for a more reliable attachment of supplemental hair for exemplary long-term performance.

It is to be understood that the above detailed description of preferred embodiments of the invention is provided by way of example only. Various details of design, construction and procedure may be modified without departing from the true spirit and scope of the invention as set forth in the appended claims.

The embodiments of the invention in which an exclusive property or privilege is claimed are defined as follows:

1. A fitting for placement at a selected location on a person's head, embedded beneath the outer surface of the person's scalp to secure the fitting at the selected location, and enable securement of hair to the person's head, the person's scalp being comprised of a depth of epidermis and derma spaced from the bone of the person's skull by an interpositioned depth of subcutaneous cellular tissue and muscle tissue, the fitting comprising:

a base member extending in longitudinal and lateral directions for placement between the outer surface of the scalp and the depth of subcutaneous cellular tissue and muscle tissue, and above the underlying bone of the person's skull, the base member having a unitary construction comprised of a resiliently flexible first synthetic polymeric material and including an integral flange for being spaced a first altitudinal distance from the outer surface and a second altitudinal distance from the bone, the first altitudinal distance corresponding substantially to the depth of epidermis and derma, and the second altitudinal distance corresponding substantially to the depth of subcutaneous cellular tissue and muscle tissue, and a post integral with the flange and extending along an altitudinal axis from the flange to an apical end, the post having a length corresponding substantially to the first altitudinal distance, the flange being resiliently flexible for selective folding away from a deployed position, wherein the flange extends radially with respect to the altitudinal axis, to a folded position, wherein the flange extends substantially parallel to the altitudinal axis, with a resilient biasing force biasing the flange toward the deployed position, for facilitating insertion of the base member through a minimal incision in the scalp, and subsequent return of the flange to the deployed position wherein the length of the post will place the entire flange in juxtaposition with the derma of the scalp, beneath the derma, with the entire flange spaced away from the bone of the skull by the depth of subcutaneous tissue and muscle tissue, and with the apical end of the post in juxtaposition with the outer surface of the scalp; and a filament extending from the apical end of the post to establish a loop projecting altitudinally from the post, the loop providing an open path extending in lateral directions, the filament being comprised of a flexible second synthetic polymeric material so as to be flexible relative to the post, such that upon embedding the base member beneath the outer surface of the scalp, the loop will project altitudinally from the scalp for reception of a ligature for securing hair to the fitting, with the loop being capable of flexing while the post remains stationary, and the apical end located in substantial juxtaposition with the outer surface of the scalp.

2. The fitting of claim 1 wherein the filament has first and second ends, at least one of the first and second ends being anchored to the base member.

3. The fitting of claim 2 wherein both the first and second ends of the filament are anchored to the base member.

4. The fitting of claim 1 wherein the base member is comprised of a high-consistency silicone, and the filament is comprised of a polypropylene surgical suture material.

5. The fitting of claim 4 wherein the filament includes first and second ends, and a surgeon's knot adjacent the first and second ends securing the filament to the base member.

6. The fitting of claim 1 wherein the base member extends in the longitudinal direction over about 0.12 inch such that upon embedding the base member beneath the outer surface of the scalp and return of the flange to the deployed position, the flange will be located about 0.12 inch below the outer surface of the person's scalp, with the entire flange spaced away from the underlying bone by the depth of subcutaneous cellular tissue and muscle tissue.

7. A method for securing supplemental hair to a person's head, along the outer surface of the person's scalp, to create an enhanced natural appearance independent of any natural hair on the person's head, the person's scalp being comprised of a depth of epidermis and derma spaced from the bone of the person's skull by an interpositioned depth of subcutaneous cellular tissue and muscle tissue, the method comprising:

selecting at least one strategic location on the person's head;

placing at least one fitting at the selected one strategic location, the fitting including a base member extending in longitudinal and lateral directions, the base member having a unitary construction comprised of a resiliently flexible first synthetic polymeric material and including a flange, and a post integral with the flange and extending along an altitudinal axis from the flange to an apical end, the post having a predetermined length corresponding substantially to the depth of epidermis and derma, the flange being resiliently flexible for selective folding away from a deployed position, wherein the flange extends radially with respect to the altitudinal axis, to a folded position, wherein the flange extends substantially parallel to the altitudinal axis, with a resilient biasing force biasing the flange toward the deployed position, and a filament extending from the apical end of the post to establish a loop projecting altitudinally from the post, the loop providing an open path extending in lateral directions, the filament being comprised of a flexible second synthetic polymeric material so as to be flexible relative to the post;

folding the flange from the deployed position to the folded position;

then, with the flange in the folded position, inserting the fitting through the person's scalp so as to place the flange beneath the outer surface of the person's scalp with the flange located between the outer surface of the scalp and the subcutaneous cellular tissue and muscle tissue above the underlying bone of the person's skull, juxtaposed with the derma of the scalp and with the entire flange spaced above the underlying bone by the interpositioned depth of subcutaneous cellular tissue and muscle tissue;

subsequently allowing the flange to return to the deployed position, in response to the resilient biasing force, to secure the fitting at the selected strategic location, with the flange juxtaposed with the derma of the scalp, beneath the derma, with the entire flange spaced from the bone of the skull by the interpositioned depth of subcutaneous cellular tissue and muscle tissue, with the apical end of the post placed in juxtaposition with the outer surface of the scalp, and with the filament projecting altitudinally from the scalp to expose the loop for reception of a ligature;

juxtaposing supplemental hair with the loop;

passing a ligature along the open path through the loop; and securing the juxtaposed supplemental hair to the filament with the ligature.

8. The method of claim 7 wherein the flange of the base member, when in the folded position, presents a predetermined diametric span, and the method includes:

making an incision in the scalp, the incision having a length substantially corresponding to the predetermined diametric span of the flange when in the folded position; and inserting the flange of the base member through the incision until the base member is embedded beneath the outer surface of the scalp, with the flange placed beneath and in juxtaposition with the derma of the scalp and the entire flange spaced above the underlying bone by the depth of subcutaneous cellular tissue and muscle tissue.

9. The method of claim 8 wherein the incision is made to a depth below the epidermis and through the derma of the scalp, the incision having a depth corresponding substantially to the depth of the epidermis and derma so that the incision is spaced above the underlying bone of the person's skull by the depth of subcutaneous cellular tissue and muscle tissue, such that upon embedding of the flange of the base member, the base member is secured beneath the outer surface of the scalp, with the flange spaced from the outer surface by the depth of epidermis and derma and the entire flange spaced above the underlying bone by the depth of subcutaneous cellular tissue and muscle tissue.

10. The method of claim 9 including closing the incision over the flange and around the post, subsequent to embedding the base member.

11. The method of claim 7 wherein the base member extends in the longitudinal direction over about 0.12 inch such that upon embedding the flange beneath the outer surface of the scalp and return of the flange to the deployed position, the flange will be located about 0.12 inch below the outer surface of the person's scalp, with the entire flange spaced away from the underlying bone by the depth of subcutaneous cellular tissue and muscle tissue.

12. The method of claim 7 including constructing the base member of a high-consistency silicone, and constructing the filament of a polypropylene surgical suture material.

13. The method of claim 12 including securing the filament to the base member with a surgeon's knot.

\* \* \* \* \*